United States Patent [19]

Chiou et al.

[11] Patent Number: 5,149,866
[45] Date of Patent: Sep. 22, 1992

[54] PROCESS FOR THE PREPARATION OF OMEGA-ARYLALKANOIC ACIDS

[75] Inventors: Huh-Sun Chiou, Corpus Christi, Tex.; Mark R. Rubino, Monroeville, Pa.; Susan W. Jahoda; Daniel Lindley; John R. Battler, all of Corpus Christi, Tex.

[73] Assignee: Hoechst Celanese Corporation, Somerville, N.J.

[21] Appl. No.: 746,276

[22] Filed: Aug. 14, 1991

[51] Int. Cl.$^5$ .................... C07C 65/01; C07C 327/00
[52] U.S. Cl. .................... 562/478; 562/405; 564/74
[58] Field of Search .................... 562/405, 478; 564/74

[56] References Cited

U.S. PATENT DOCUMENTS

| | | | |
|---|---|---|---|
| 2,459,706 | 1/1949 | King | 260/561 |
| 2,489,348 | 11/1949 | Wenner | 260/515 |
| 2,610,980 | 9/1952 | Naylor | 260/558 |
| 2,689,246 | 9/1954 | Feichtinger | 260/247.1 |

FOREIGN PATENT DOCUMENTS

| | | | |
|---|---|---|---|
| 747961 | 12/1966 | Canada | 260/558 |
| 405675 | 11/1924 | Fed. Rep. of Germany | 120/16 |

OTHER PUBLICATIONS

Karl Kindler, D.R.P. 405675 cl. 120 (1924).
J. Amer. Chem. Soc., 68, pp. 2633-2634 (1946).
R. Adam, Ed., *Organic Reactions*, vol. III pp. 83-107, New York, John Wiley (1946).
Synthesis, Jun. 1975, pp. 358-375 (1975).
C. G. Johsi: J. Sci. Ind. Res. (India) 21B, pp. 284-285 (1962).
F. Asinger et al., in Monatschefte fur Chemie, 103, pp. 1661-1668 (1972) (German version and English translation included).

*Primary Examiner*—Jose G. Dees
*Assistant Examiner*—Porfirio Nazario
*Attorney, Agent, or Firm*—Elliott Korsen; Donald R. Cassady

[57] ABSTRACT

The present inventon pertains to a process for the preparation of omega-arylalkanoic acids of the genral formula $$R-Ar-R^1-COOH$$

wherein R is hydrogen, hydroxy, $C_1$-$C_8$ alkyl, $C_1$-$C_8$ alkoxy, or aryl; wherein $R^1$ is $C_1$-$C_4$ alkyl; and wherein Ar is an aryl group which can be further substituted with at least one of hydroxy, $C_1$-$C_8$ alkyl, $C_1$-$C_8$ alkoxy, aryl, halide, amino, or acetamido. The omega arylalkanoic acids of the given formula are prepared using catalysts which provide an improvement over the known Willgerodt-Kindler reaction.

The present invention also pertains to methods for removing sulfur during the above-described process for the preparation of the omega-arylalkanoic acids.

17 Claims, No Drawings

PROCESS FOR THE PREPARATION OF OMEGA-ARYLALKANOIC ACIDS

BACKGROUND OF THE INVENTION

1. Field of the Invention

The present invention relates to a process for the preparation of omega-arylalkanoic acids of the general formula.

$$R-Ar-R^1-COOH$$

wherein

R is hydrogen, hydroxy, $C_1-C_8$ alkyl, $C_1-C_8$ alkoxy, or aryl;

$R^1$ is $C_1-C_4$ alkyl; and

Ar is an aryl group which can be further substituted with at least one of hydroxy, $C_1-C_8$ alkyl, $C_1-C_8$ alkoxy, aryl, amino with the amino nitrogen bonded to hydrogen or $C_1-C_8$ alkyl, or acetamido.

More particularly, this invention relates to an improved process for the preparation of omega-arylalkanoic acids via the Willgerodt-Kindler reaction and to methods of removing sulfur from the product produced by this improved process.

2. Background Information and Description of the Related Art

Omega-arylalkanoic acids are useful intermediates in the production of various chemicals and pharmaceuticals. For example, 4'-methoxyphenylacetic acid is an intermediate in the production of dextromethorphan, anti-cough medicine; homoveratic acid, obtained from 3,4-dimethoxyacetophenone (DMAP) is an important pharmaceutical intermediate; and 4-biphenylacetic acid, an analgesic, is produced from 4-acetylbiphenylacetophenone.

The omega-arylalkanoic acids can be synthesized from a thioamide which is produced via the Willgerodt-Kindler reaction. The thioamide can be synthesized by reaction of an aryl alkyl ketone or other starting material, sulfur and a primary or secondary amine. Following the preparation of the thioamide, it can be hydrolyzed to the corresponding omega-arylalkanoic acid.

The Willgerodt reaction is well known in the art as the reaction between an aryl alkyl ketone aqueous ammonium polysulfide to produce an aromatic amide and/or ammonium salt of the corresponding acid.

In addition to aryl alkyl ketones, the reaction has been shown to be applicable to the production of amides from other compounds such as dialkyl ketones, aliphatic mercaptans, secondary and tertiary alcohols, acetals and aromatic hydrocarbons. It is also known that a mixture of sulfur and ammonia is equivalent to ammonium polysulfide in obtaining the reaction.

In the Kindler modification of the Willgerodt reaction, an aryl alkyl ketone or other reactant can be reacted with sulfur and a primary or secondary amine such as morpholine and the product is the thioamide.

C. G. Joshi, in J. Sci. Ind. Res., 21B, 1962, 284-5, discloses a method for the preparation of arylacetic acids from aryl-alkyl ketones by a modification of the Willgerodt-Kindler reaction. This process involves the use of morpholine and sulfur in reflux with the ketone, followed by basification, cooling, filtration and acidification. However, this article does not disclose the use of a catalyst or the sulfur removal techniques disclosed in this application.

U.S. Pat. No. 2,489,348 issued Nov. 29, 1949 to Wenner discloses the production of arylacetic acids and amides. Some examples disclose the purification of the crude acids by basification, filtering and acidification to yield the free acids. However, the production method disclosed does not employ sulfur nor function in the manner of the Willgerodt-Kindler reaction.

F. Ansinger et al., in Monatshefte für Chemie, 103, 1972, 1661-1668, disclose to the preparation of various materials comprising sulfur, nitrogen and aryl components, wherein acetophenone is treated with sulfur and amines. In particular, hexathiocanethiones were obtained by treating $RC_6H_4COMe$ with $R'NH_2$ and S in the presence of HOAc.

SUMMARY OF THE INVENTION

In accordance with the present invention, a process is provided for the preparation of omega-arylalkanoic acids. More particularly, a process is provided for the preparation of omega-arylalkanoic acids via an improved Willgerodt-Kindler reaction which employs various catalysts which surprisingly improve the yield of the thioamide precursor of the acid product. Use of the catalysts also significantly decreases the amount of sulfur necessary to convert the starting material to the thioamide as well as the reaction pressure generated during the reaction. Additionally, a process is provided for the separation of the omega-arylalkanoic acid product from sulfur and other sulfur-containing compounds which are generated as part of the Willgerodt-Kindler reaction.

In view of the above, it is an object of the invention to prepare omega-arylalkanoic acids in high yield under conditions wherein less sulfur is employed.

It is another object of the invention to prepare omega-arylalkanoic acids which are more easily isolated from sulfur and other sulfur-containing compounds.

It is a further object of this invention to economically prepare omega-arylalkanoic acids via the Willgerodt-Kindler reaction which can be commercially useful in the preparation of chemicals and pharmaceutical intermediates.

It is a further object of the invention to prepare omega-arylalkanoic acids which are essentially free from contamination by sulfur and other sulfur-containing compounds such as methyl mercaptan, dimethyl sulfide, and dimethyl disulfide by a separation process which removes residual sulfur and sulfur-containing compounds by careful control of the pH during the acidification step and by prolonged thermal-treatment prior to and during a vacuum distillation step.

DETAILED DESCRIPTION TO THE INVENTION

The reaction carried out by the process of the invention is shown in the following steps:

| Sulfur (eq.) | DMA (eq.) | HOAc (eq.) | Time | Yield | PSIG Max. |
|---|---|---|---|---|---|
| 2.5 | 2.3 | 1.1 | 1 | 89 | 107 |
| 2.5 | 2.3 | 0.0 | 1 | 51 | 138 |
| 2.5 | 2.3 | 1.1 | 2 | 91 | 112 |
| 2.5 | 2.3 | 0.0 | 2 | 63 | 150 |
| 1.3 | 1.5 | 0.5 | 2 | 70 | 120 |
| 1.3 | 1.5 | 0.0 | 2 | 52 | 149 |
| 1.3 | 2.0 | 0.5 | 2 | 75 | 123 |

-continued

| Sulfur (eq.) | DMA (eq.) | HOAc (eq.) | Time | Yield | PSIG Max. |
|---|---|---|---|---|---|
| 1.3 | 2.0 | 0.0 | 2 | 48 | 140 |

In the above reactions the substituents R, $R^1$, $R^2$, $R^3$ and M are defined as follows:

R is hydrogen, hydroxy, $C_1$–$C_8$ alkyl, $C_1$–$C_8$ alkoxy, or aryl;

$R^1$ is $C_1$–$C_4$ alkyl;

$R^2$ is hydrogen or alkyl;

$R^3$ is hydrogen or alkyl, so long as both $R^2$ and $R^3$ are not both hydrogen;

Ar is an aryl group which can be further substituted with at least one of hydroxy, $C_1$–$C_8$ alkyl, $C_1$–$C_8$ alkoxy, aryl, halide, amino, or acetamido; and, M is an alkali metal selected from the group consisting of Na, K and Li, wherein the base of step II is comprised of said alkali metal.

Ar may be, for example, phenyl, 1-naphthyl, 2-naphthyl, 4-biphenyl, 2-phenanthryl, 1-pyrenyl or 2-benzyloxyphenyl with these groups being unsubstituted or having at least one ring hydrogen atom substituted with hydroxy; $C_1$–$C_8$ alkyl; $C_1$–$C_8$ alkoxy; aryl; halide, including chloride, bromide, iodide and fluoride; amino with the amino nitrogen bonded to hydrogen or $C_1$–$C_8$ alkyl, or acetamido. In general, it is preferred that not more than two ring atoms are substituted. Phenyl is the preferred aryl group.

In Step I, the aryl alkyl ketone, sulfur, and amine, along with a catalyst selected from acetic acid, acetic anhydride, sulfuric acid, hydrogen sulfide dimethylacetamide, dimethylformamide and sodium sulfate are reacted to form a thioamide intermediate:

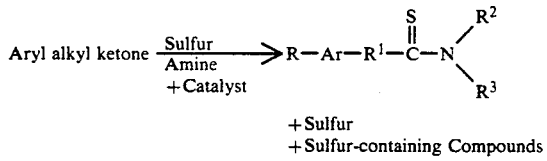

+ Sulfur
+ Sulfur-containing Compounds wherein R and $R^1$ are as previously described, and where $R_2$ and $R_3$ are hydrogen or alkyl, so long as $R_2$ and $R_3$ are not both hydrogen. The use of the catalyst results in a reduction in the amount of sulfur that is necessary in the Willgerodt-Kindler reaction of the ketone, and results in improved yield over that previously known in the art.

The amine used in Step 1 is selected from primary and secondary amines, such as, for example, methylamine, dimethylamine, diethylamine, morpholine and pyrrolidine.

In carrying out the method of this invention, sulfur may be initially present in an amount of about 0.5 to 10 moles per mole of ketone. A preferred ratio is about 1 to 5 moles with a most preferred molar ratio of about 1.3 to 2.5.

No solvent need be initially employed in the Willgerodt-Kindler reaction portion of the invention. However, it is advantageous in some instances to have a solvent present. For instance, a solvent may be necessary to aid in the stirring of the reaction mixture. The choice of solvent will depend largely on the solubilities of the reactants.

The reaction can be carried out at a temperature in the range of 110° C. to 180° C., preferably in a range of 120° C.–150° C.; most preferably about 130° C.–140° C.

The use of the catalyst results in a faster reaction rate and can result in a reduction in the pressure which occurs during the reaction. The pressure (psig) is not critical, but is permitted to increase as dictated by other reaction parameters. Typical reaction pressures range from about 30 psig–200 psig.

The catalyst employed can be present in an amount that depends largely on the amount of ketone, sulfur and amine present in the reaction. The ratio of catalyst to sulfur is typically in the range of 1 equivalent of catalyst to 1–10 equivalents of sulfur. A preferred ratio is 1 equivalent of catalyst to 2–4 equivalents of sulfur. The typical ratio of sulfur to amine ranges from about 1 equivalent of sulfur to 0.1–3 equivalents of amine.

In Step II, the base hydrolysis of the thioamide can be accomplished by using an alkali metal base such as sodium, potassium, or lithium hydroxide in a large quantity of water. Typically, the hydroxide solution ranges from about 10%–50% by weight alkali metal base, preferably 20%–30% by weight alkali metal base. The resultant reaction mixture typically exhibits a pH>11. The base employed is preferably sodium hydroxide. At this step the sulfur containing compounds include the alkali metal base sulfide, which is later converted to hydrogen sulfide, in Step III, for easier removal.

Step III and IV are optional in the formation of the omega-arylalkanoic acid and are for the purpose of removing sulfur from the reaction medium. After Step IV, an additional optional step can be included wherein the reaction medium is treated with activated carbon to remove color bodies, some fine sulfur particles and sulfur-containing compounds, which may have been formed during the process through Step IV.

In Step III, the pH of the solution can be adjusted by addition of hydrochloric, sulfuric, phosphoric or other suitable acids, which results in the formation of $H_2S$ which can subsequently be removed from the reaction mixture by purging of the mixture with an inert gas such as nitrogen, for example. Additionally much of the bulk sulfur remaining from the Willgerodt-Kindler reaction precipitates out. It has been found that the solubility of sulfur in aqueous solution greatly decreases as concentration of the sulfur-containing compounds such as the sulfides decreases. Therefore, as these sulfur-containing compounds are removed by the pH adjustment of Step III, followed by inert gas purging of the reaction mixture, the sulfur precipitates out of the solution and can be removed by filtration, centrifugation or similar, known-in-the-art separation methods. The pH of the solution in this step is adjusted, using an acid, to a range of between 1 and 7, preferably to a pH range of 6–6.5, since the R—Ar—$R^1$—$CO_2M$ tends to precipitate out of solution at a pH of less than about 6.

If the pH of the reaction mixture is adjusted below about 6.0 in Step III (during the conversion of $M_2S$ to $H_2S$, prior to the Step IV Sulfur Removal, the pH must be readjusted to greater than about 6, to ensure that the omega-arylalkanoic acid salt will be in solution (and not removed with the sulfur in Step IV).

Following the above-described pH adjustment, the system is purged with a inert gas such as nitrogen or argon to further remove $H_2S$ and other sulfur-containing compounds and to precipitate out the sulfur.

In Step IV, the bulk sulfur can be removed by methods known in the art to leave primarily the omega-arylalkanoic acid salt in the reaction solution. Following the Step IV removal of the bulk sulfur, the remaining salt is acidified in Step V, to convert the salt to the desired omega-arylalkanoic acid product. The acidified reaction solution is acidified to a pH of about 4 or less using an acid such as a mineral acid. The crude omega-arylalkanoic acid product can then be separated from the aqueous reaction solution by at least two techniques. When the reaction medium is acidified to a pH of less than about 4, if the reaction medium temperature is about 60° C. or less, the crude product precipitates from the aqueous reaction medium. If the reaction medium temperature is greater than about 60° C. (eg. 70° C. or more), two phases are formed, an organic phase containing the crude product and an aqueous phase; the crude product can then be decanted from the aqueous phase. Use of the precipitation technique provides more complete crude product recovery, but requires more time. The product is subsequently, optionally subjected to high temperature vacuum distillation in Step VI, to remove residual sulfur and sulfur-containing compounds. This distillation step is typically carried out at a temperature ranging from about 180° C. to 210° C., at a vacuum ranging from about 5 mm Hg-10 mm Hg, for a time period of about 6 to about 20 hours. During distillation, a high reflux ratio is maintained during removal of the light ends which are distilled off prior to the omega-arylalkanoic acid product. Light ends removal can require a distillation time period ranging from about 6 to about 20 hours. During removal of the light ends, significant quantities of sulfur-containing compounds are decomposed and carried off with the light ends. Some sulfur-containing compounds also remain in the bottoms, with the desired omega-arylalkanoic acid product containing less than about 100 ppm of total sulfur (total sulfur being only the sulfur portion of sulfur-containing compounds). Typically, total sulfur in the omega-arylalkanoic acid product ranges from about 25 ppm to about 80 ppm.

There are other methods which can be used to separate the omega-arylalkanoic acid product from the organic portion of the reaction mixture, such as crystallization.

The inventive method may be further illustrated by the following examples:

EXAMPLE 1

Preparation of 4'-Methoxyphenylacetic Acid 420 g (2.8 mol) of 4-methyacetophenone (4-MAP) was heated between 120° C. and 160° C. for 3 to 4 hours in the presence of 116.5 g (3.6 mol) of sulfur in 189 g (4.2 mol) of dimethylamine and 84 g (1.4 mol) of acetic acid. Typical reaction pressure at about 160° C. was 90-95 psig. The resultant thioamide reaction mixture was cooled to room temperature, and 896 g of 50 wt% NaOH solution, along with 896 g of H2O were charged to the reaction mixture. The mixture was heated under reflux (105° C.-110° C.) for 3 to 4 hours. After cooling, the pH value of the reaction medium was adjusted to 6.0 to 6.5 by addition of HCl. Hydrogen sulfide was observed to be liberated vigorously during the pH adjustment of the reaction medium. Nitrogen was then sparged through the reaction medium until the residual hydrogen sulfide had been reduced to less than 10 ppm. The removal of H2S and other sulfur-containing compounds resulted in the precipitation of the majority of excess sulfur which was subsequently removed by filtration. The aqueous filtrate was treated with activated carbon at room temperature for one hour to further remove fine sulfur particles, sulfur-containing compounds and other color bodies.

The resultant aqueous solution was acidified to pH<4 with HCl, at a temperature of 60° C., to precipitate out the crude product, which was subsequently separated from the aqueous solution by filtration.

The above-described, precipitated crude 4'-methoxyphenylacetic acid, containing about 15% to 20% water, was heated at 180°-200° C. under vacuum (typically 5 mmHg-20 mmHg). The water distilled off immediately, with light ends being recovered over a time period of up to about 18 hours. During the light ends removal, residual sulfur and sulfur-containing compounds were also removed. The 4'-methoxypehnylacetic acid product was distilled off after light ends removal. Two hundred and sixty (260) g (1.57 mol) of 4'methoxypehnylacetic acid was obtained, which contained less than 100 ppm of total sulfur.

EXAMPLE 2

Preparation of 4'-Hydroxyphenylpropionic Acid

To a one gallon autoclave reactor is charged 420 g (2.8 mol) of 4'-hydroxyphenylpropiophenone, 116.5 g (3.6 mol) of sulfur, 84 g (1.4 mol) of acetic acid and 189 g (4.2 mol) of dimethylamine. The procedure described in Example 1 is followed and 4'-hydroxyphenylacetic acid product containing less than 100 ppm of total sulfur is obtained.

EXAMPLE 3

Preparation of 4'-Butoxyphenylacetic Acid

To a one-gallon autoclave reactor is charged 537.6 g (2.8 mol) of 4'-butoxyacetophenone, 116.5 g (3.6 mol) sulfur, 84 g (1.4 mol) acetic acid and 189 g (4.2 mol) dimethylamine. The procedure described in Example 1 is followed and 4'-butoxyphenylacetic acid product containing 3 less than 100 ppm of total sulfur is obtained.

Reactions run under similar conditions to those described in Example 1 are reported below in Tables 1-5. The starting material and the catalysts used were varied to show the effectiveness of the process employing various catalysts versus the uncatalyzed reactions.

TABLE 1

The starting ketone for this series of experiments was acetophenone, sulfur equivalents were 1.3, dimethylamine equivalents were 1.5. The temperature for each run was 130° C.

| (HOAc) Acetic Acid (eq.) | Time (hr.) | Yield | PSIG Max. |
|---|---|---|---|
| 0.5 | 2 | 87 | 95 |
| 0.0 | 2 | 55 | 134 |
| 0.5 | 1 | 93 | 75 |
| 0.0 | 1 | 72 | 175 |

TABLE 2

The starting material was 3,4-dimethoxyacetophenone (DMAP); the thioamide formed from DMAP is a precursor of homoveratric acid, an important pharmaceutical intermediate. The temperature for each run was 130° C. and the reaction time was 1 hour.

| Sulfur (eq.) | DMA (eq.) | HOAc (eq.) | Yield | PSIG |
|---|---|---|---|---|
| 2.5 | 1.5 | 1.1 | 79 | 40 |
| 2.5 | 1.5 | 0.0 | 30 | 150 |
| 1.3 | 1.5 | 0.5 | 68 | 68 |
| 1.3 | 1.5 | 0.0 | 51 | 145 |

TABLE 3

The starting material was 4-acetylbiphenyl; the thioamide formed from which is a direct precursor of a 4-biphenylacetic acid, an analgesic drug. A solvent, t-butyl methyl ether, was employed to aid stirring. The temperature for each run was 130° C.

| Sulfur (eq.) | DMA (eq.) | HOAc (eq.) | Time | Yield | PSIG Max. |
|---|---|---|---|---|---|
| 2.5 | 2.3 | 1.1 | 1 | 89 | 107 |
| 2.5 | 2.3 | 0.0 | 1 | 51 | 138 |
| 2.5 | 2.3 | 1.1 | 2 | 91 | 112 |
| 2.5 | 2.3 | 0.0 | 2 | 63 | 150 |
| 1.3 | 1.5 | 0.5 | 2 | 70 | 120 |
| 1.3 | 1.5 | 0.0 | 2 | 52 | 149 |
| 1.3 | 2.0 | 0.5 | 2 | 75 | 123 |
| 1.3 | 2.0 | 0.0 | 2 | 48 | 140 |

TABLE 4

Various hydrocinnamic acids which are of commercial value, can also be prepared by the Willgerodt-Kindler reaction of propiophenones, followed by hydrolysis. As shown below, acetic acid improves the yield when 4-methoxypropiophenone is used as the starting ketone. The temperature for each run was 130° C. and the reaction time was 2 hours.

| Sulfur (eq.) | DMA (eq.) | HOAc (eq.) | Yield | PSIG Max. |
|---|---|---|---|---|
| 2.5 | 1.5 | 1.1 | 75 | 26 |
| 2.5 | 1.5 | 1.1 | 70 | 34 |
| 2.5 | 1.5 | 0.0 | 55 | 79 |
| 1.3 | 1.5 | 0.5 | 70 | 59 |
| 1.3 | 1.5 | 0.0 | 61 | 130 |

TABLE 5

This series of experiments demonstrates the use of Step I catalysts other than acetic acid. The arylalkyl ketone starting material was 4'-methoxyacetophenone. The reaction temperature for each experiment was about 130° C.

| Reaction Time | Sulfur (eq.) | DMA (eq.) | Catalyst (eq.) | Pressure (PSIG) | Yield % |
|---|---|---|---|---|---|
| 4 | 2.5 | 1.9 | 0 | 47 | 77 |
| 4 | 2.5 | 1.9 | H$_2$S (0.25) | 54 | 83 |
| 4 | 2.5 | 1.9 | dimethylacetamide (1.0) | 35 | 85 |
| 4 | 2.5 | 1.9 | dimethylformamide (1.0) | 45 | 82 |
| 2 | 2.5 | 2.0 | Na$_2$SO$_4$ (0.55) | 60 | 88 |
| 2 | 2.5 | 4.0 | acetic anhydride (1.1) | 36 | 92 |
| 2 | 2.5 | 3.0 | sulfuric acid (0.55) | 76 | 88 |

The embodiments described above are not intended to place undue limitations on the scope of the present invention, particularly regarding non-critical features of the invention, wherein one skilled in the art can make modifications which provide obvious variations of the invention. Such variations are intended to fall within the scope of the present invention, particularly regarding non-critical features of the invention, wherein one skilled in the art can make modifications which provide obvious variations of the invention. Such variations are intended to fall within the scope of the present invention as defined in the following claims.

What is claimed is:

1. A process for the preparation of omega-arylalkanoic acids of the formula $$R-Ar-R^1-COOH$$

wherein

R is hydrogen, hydroxy, $C_1-C_8$ alkyl, $C_1-C_8$ alkoxy, or aryl;

$R^1$ is $C_1-C_4$ alkyl; and

Ar is an aryl group which can be further substituted with at least one of hydrogen, $C_1-C_8$ alkyl, $C_1-C_8$ alkoxy, aryl, halide, amino with the amino nitrogen bonded to hydrogen or $C_1-C_8$ alkyl, or acetamido;

said process comprising the steps of:

a) reacting an aryl alkyl ketone of the formula $$R-Ar-CO-R^1$$

wherein R, $R^1$ and Ar are as defined above, with sulfur, a primary or secondary amine and a catalyst to produce a reaction mixture containing a thioamide, sulfur and sulfur-containing compounds;

b) subsequently basifying said Step a) reaction mixture to produce a compound of the formula R—Ar—$R^1$—CO$_2$M, wherein R, $R^1$ and Ar are as defined above and M is an alkali metal selected from the group consisting of Na, K, and Li; and c) acidifying said Step b) reaction mixture to produce the omega-arylalkanoic acid of the formula R—Ar—$R^1$CO$_2$H, wherein R, $R^1$, and Ar are as defined above.

2. The process of claim 1 wherein said Step a) catalyst is selected from the group consisting of acetic acid, acetic anhydride, sulfuric acid, hydrogen sulfide, dimethylacetamide, dimethylformamide, and sodium sulfate.

3. The process of claim 1, wherein the amine is selected from methylamine, dimethylamine, diethylamine, morpholine and pyrrolidine.

4. The process of claim 2, wherein the base used in Step b) is selected from sodium or potassium hydroxide.

5. The process of claim 1, wherein the acid used in Step c) is selected from hydrochloric, sulfuric or phosphoric acid.

6. A process for the preparation of omega-arylalkanoic acids of the formula $$R-Ar-R^1-COOH$$

wherein

R is hydrogen, hydroxy, $C_1-C_8$ alkyl, $C_1-C_8$ alkoxy, or aryl;

$R^1$ is a $C_1-C_4$ alkyl; and

Ar is an aryl group which can be further substituted with at least one of hydroxy; $C_1-C_8$ alkyl; $C_1-C_8$ alkoxy; aryl, halide; amino with the amino nitrogen bonded to hydrogen or $C_1$-$C_8$ alkyl; or acetamido; said process comprising the steps of:

a) reacting an arylalkylketone of the formula $$R-Ar-CO-R^1$$

wherein R, $R^1$ and Ar are as defined above, with sulfur, and a primary or secondary amine, to produce a reaction mixture containing a thioamide, sulfur and sulfur-containing compounds;

b) subsequently basifying the Step a) reaction mixture to produce a compound of the formula R—Ar—$R^1$—$CO_2M$, wherein R, $R^1$ and Ar are as defined above and M is an alkali metal selected from the group consisting of Na, K and Li;

c) adjusting the pH of the reaction product mixture of Step b) using an acid, until the pH of said mixture ranges between 1 and 7;

d) purging the pH-adjusted mixture of Step c) using inert gas to remove hydrogen sulfide;

e) separating sulfur from the pH-adjusted, inert gas-purged mixture of Step d); and f) acidifying the resultant solution after Step e) to convert R—Ar—$R^1$—$CO_2H$ wherein R, $R^1$, and Ar are as defined above.

7. The process of claim 6, wherein a catalyst is used in Step a), whereby yield of said thioamide is improved.

8. The process of claim 6 or claim 7, wherein the pH of said mixture after Step c) ranges from 6-7.

9. The process of claim 6 or claim 7, wherein the pH of said mixture after Step c) ranges from about 1 to less than 6, and wherein, after said Step d) purging with inert gas, a base is added to increase the pH of said mixture to 6 or greater prior to said Step e) separation.

10. The process of claim 6 or claim 7, wherein said Step f) acidification is carried out until the pH of said reaction medium is less than about 4.

11. The process of claim 10, wherein the temperature of said reaction medium is adjusted to about 60° C. or less, whereby crude omega-arylalkanoic acid product is precipitated from said reaction medium.

12. The process of claim 10 wherein the temperature of said reaction medium is adjusted to greater than about 60° C., whereby a two-phase reaction medium is formed, followed by decantation of an organic phase containing omega-arylalkanoic acid product from an aqueous phase.

13. The process of claim 11, wherein said precipitated crude omega-arylalkanoic acid is separated from said reaction medium by filtration or centrifugation.

14. A method for removing sulfur and sulfur-containing compounds from said crude omega-arylalkanoic acid product produced by the process of claim 12, wherein said crude product is distilled at a temperature ranging from about 180° C. to about 210° C. for a time period sufficient to remove light ends from the crude product, followed by separation of the omega-arylalkanoic acid from remaining bottoms, whereby sulfur-containing compounds are removed from said omega-arylalkanoic acid.

15. The method of claim 14, wherein the total sulfur remaining in said omega-arylalkanoci acid is less than about 100 ppm.

16. A method for removing sulfur and sulfur-containing compounds from said crude omega-arylalkanoic acid product produced by the process of claim 13, wherein said crude product is distilled at a temperature ranging from about 180° C. to about 210° C. for a time period sufficient to remove light ends from said crude product, followed by separation of the omega-arylalkanoic acid from remaining bottoms, whereby sulfur-containing compounds are removed from said omega-arylalkanoic acid.

17. The method of claim 15, wherein the total sulfur remaining in said omega-arylalkanoic acid is less than about 100 ppm.

* * * * *

UNITED STATES PATENT AND TRADEMARK OFFICE
CERTIFICATE OF CORRECTION

PATENT NO.   :   5,149,866

DATED        :   September 22, 1992

INVENTOR(S)  :   Huh-Sun Chiou; Mark R. Rubino; Susan W. Jahoda;
                 Daniel Lindley; and John R. Battler It is certified that error appears in the above—identified patent and that said Letters Patent is hereby corrected as shown below:

In column 2, lines 60-69 and in column 3, lines 1-5 delete the tabled subject matter on all these lines and insert in place thereof the reaction subject matter (Formula I-VI) described in the attachment.

UNITED STATES PATENT AND TRADEMARK OFFICE
CERTIFICATE OF CORRECTION

PATENT NO. : 5,149,866
DATED : September 22, 1992
INVENTOR(S) : Huh-Sun Chiou; Mark R. Rubino; Susan W. Jahoda; Daniel Lindley; and John R. Battler It is certified that error appears in the above-indentified patent and that said Letters Patent is hereby corrected as shown below:

I. Improved Willgerodt-Kindler Reaction

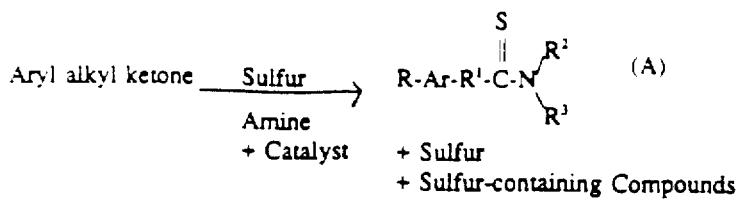

II. Base Hydrolysis

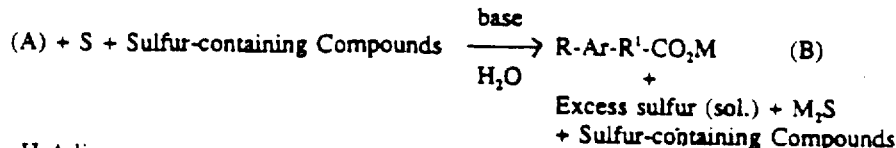

III. pH Adjustment

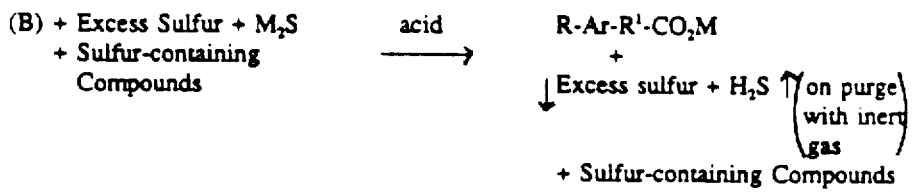

UNITED STATES PATENT AND TRADEMARK OFFICE
CERTIFICATE OF CORRECTION

PATENT NO. : 5,149,866
DATED : September 22, 1992
INVENTOR(S) : Huh-Sun Chiou; Mark R. Rubino; Susan W. Jahoda; Daniel Lindley; and John R. Battler It is certified that error appears in the above-indentified patent and that said Letters Patent is hereby corrected as shown below:

IV. Sulfur Removal

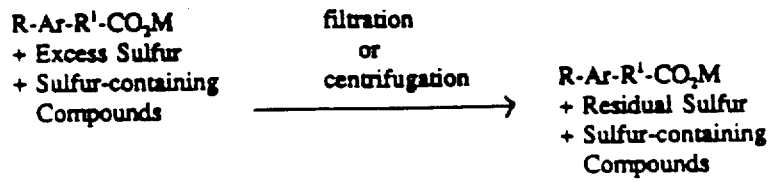

V. Acidification

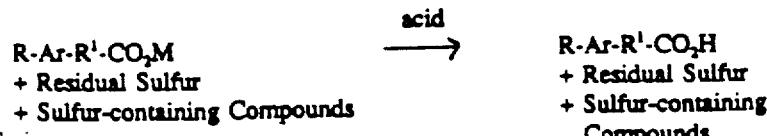

VI. Distillation

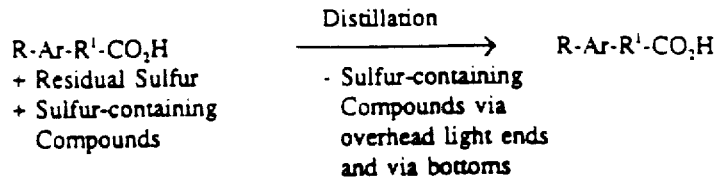

Signed and Sealed this

Fifth Day of October, 1993

Attest:

BRUCE LEHMAN

Attesting Officer

Commissioner of Patents and Trademarks